(12) United States Patent
Garland

(10) Patent No.: US 6,749,557 B2
(45) Date of Patent: Jun. 15, 2004

(54) SELF LUBRICATING SEX AIDS

(75) Inventor: Lawrence B. Garland, Boulder, CO (US)

(73) Assignee: E.T.C., Inc., Boulder, CO (US)

( * ) Notice: Subject to any disclaimer, the term of this patent is extended or adjusted under 35 U.S.C. 154(b) by 144 days.

(21) Appl. No.: 10/261,995

(22) Filed: Sep. 30, 2002

(65) Prior Publication Data

US 2003/0171647 A1 Sep. 11, 2003

Related U.S. Application Data

(60) Provisional application No. 60/362,862, filed on Mar. 8, 2002.

(51) Int. Cl.$^7$ .............................. A61F 5/00; A61H 1/00
(52) U.S. Cl. ............................................ 600/38; 601/80
(58) Field of Search ..................... 600/38–41; 601/46, 601/55, 80, 88, 89, 93, 94, 95, 112–114, 136, 137; 128/842

(56) References Cited

U.S. PATENT DOCUMENTS

| 2,369,881 A | * | 2/1945 | Berns et al. ................ 601/154 |
| 4,919,149 A | * | 4/1990 | Stang ........................... 128/842 |
| 5,470,303 A | * | 11/1995 | Leonard et al. ................ 601/84 |
| 6,350,230 B1 | * | 2/2002 | Kontos ........................ 600/38 |

* cited by examiner

Primary Examiner—Samuel G. Gilbert
(74) Attorney, Agent, or Firm—Donald W. Margolis

(57) ABSTRACT

A sex aid system modified to be self lubricating, and including a hollow chamber for carrying lubricating fluid; and a mechanism for connecting the hollow chamber to the sex aid. The sex aid includes a surface portion intended to contact the external or internal surfaces of users or a user; and one or more hole at the surface portion in fluid contact with the connecting mechanism. In use, any lubricating fluid contained in the hollow chamber may traverse through the connecting mechanism and thence through the one or more hole to the surface portion of the sex aid to thereby render the sex aid self lubricating.

10 Claims, 4 Drawing Sheets

SELF LUBRICATING SEX AIDS

RELATED APPLICATION

The present application claims the benefit under title 35, United States Code, Section ii 9(e) of U.S. provisional application No. 60/362,862, filed Mar. 8, 2002 entitled "SELF LUBRICATING SEX AIDS".

BACKGROUND OF THE INVENTION

1. Field of the Invention

The present invention relates to self lubricating sex aids for use in avoiding irritation or pain during sexual activities or during auto erotic sex activities, while concomitantly increasing the pleasure of the users or user.

2. Description of the Prior

The use of sex aids of known designs and configurations is well known in the prior art. More specifically, sex aids of known designs and configurations heretofore devised and utilized for the purpose of increasing sexual stimulation through known methods and apparatuses are known to consist basically of familiar, expected, and obvious structural configurations.

Among the large number of prior art sex aids of known designs and configurations are, by way of example, those taught in U.S. Pat. No. 5,690,603 which discloses a sexual stimulator that contains a vibrator and can include a fluid chamber that allows the flow of the fluid from part to part within the sealed chamber; U.S. Pat. No. 6,280,403 which discloses a massage device that includes a sealable chamber to include, for example, warm water, but from which chamber no fluid is allowed to flow to the skin or internal private parts of the user; and U.S. Pat. No. 6,322,493 which teaches a clitoral stimulator that directly dispenses a stimulating compound. None of these prior art systems include normally open through-holes from their chambers to the surfaces of the devices. In fact, as noted, U.S. Pat. Nos. 5,690,603 and 6,280,403 are rigorously designed to avoid allowing any fluid to exit from their chambers during use. It is also noted that during the use of many sex toys it is not unusual to apply moisturizing fluid by hand or by other mean to the skin or internal private parts of the user, thereby requiring unwanted interruptions before or distractions during such activity.

Therefore, it can be appreciated that there exists a previously unappreciated need for a new and improved sex aid that allows a lubricating fluid to exit from normally open through-holes from chambers associated with the device to the surface of the device during use for the purpose of avoiding irritation or pain during sexual activities or during auto erotic sex activities, while concomitantly serving the purpose of increasing the pleasure of the users or user during such activities.

SUMMARY OF THE INVENTION

In this respect, the sex aids according to the present invention substantially depart from the conventional concepts and designs of the prior art, and in so doing has as an object to provide various apparatus primarily developed for the purpose of avoiding irritation or pain during sexual activities or during auto erotic sex activities, while concomitantly increasing the pleasure of the users or user during sexual activity by intentionally having fluid exit through normally open through-holes from chambers associated with the device during use. In this regard, the present invention substantially fulfills a previously unappreciated need.

In view of the limitations inherent in the sex aids of known designs and configurations now known in the prior art, the present invention provides new and improved self-lubricating sex aids that allow the users or user to avoid irritation or pain during sexual activities, or during auto erotic sex activities, while concomitantly increasing the pleasure of the users or user. As such, the general purpose of the present invention, which is described in greater detail below, is to provide a new and improved self lubricating sex aids and methods which have all the advantages of the prior art and none of the disadvantages.

To attain such results, the present invention essentially comprises modifications to sex aid systems to provide new and improved systems for use in avoiding irritation or pain during sexual activities or during self stimulated sex activities, while concomitantly increasing the pleasure of the users or user. The new and improved sex aid systems uniformly comprise the modification of or addition to art known sex aid systems which provides for the self lubrication of the sex aids for the users or user, especially at the surface or surfaces of the sex aid that contact and stimulate the external or internal erotic surfaces of the users or user.

In one format, where the volume and the shape of the sex aid will allow, each new and improved sex aid system is modified to include a hollow chamber associated with the sex aid, either internal or external to the sex aid. Such new and improved sex aids, in accordance with the present invention, are further modified to include at least one or more normally open through-hole extending from the added chamber to the surface portions of each sex aid, and especially to the surface portions of each sex aid that are intended to contact and stimulate the external or internal erotic surfaces of the users or user.

In the operation of the present invention, an off the shelf water-soluble moisturizing fluid, or sterile water or other non-irritating fluid is poured into the hollow chamber. In each instance the moisturizing fluid is preferably inert to both plastic and to rubber. Each such new and improved sex aid system may be manipulated for its desired purpose by the users or user, or may include or be attached to a vibrator device or other energizing apparatus. In operation, external air pressure and the motion or vibration of each new and improved sex aid system causes the fluid present in the hollow chamber to exit through the through-hole or holes to lubricate any external or internal body parts with which the hole or holes are placed in contact.

In another format, where the volume and the shape of the sex aid will not allow it to be modified to include an internal chamber, a fluid reservoir may be provided that is either attached directly to the sex aid or remotely connected, say through a tube, but in either case to normally open through-holes to lubricate any external or internal body parts with which the hole or holes are placed in contact with the device. In such modifications in accordance with the present invention, the attached or remote reservoir is in fluid contact with the new and improved sex aids of the present invention, which sex aids are also modified to include at least one or more hole extending from connection with the reservoir to the surface portions of each such sex aid, and especially to the surface portions of each such sex aid that are intended to contact the external or internal surfaces of the users or user. Those modifications with an added external reservoir also operate in response to external air pressure and the motion or vibration of each new and improved sex aid system, to cause the fluid present in the reservoir to exit through the hole or holes to lubricate any external or internal body parts with which the hole or holes are placed in contact.

It has been determined that the preferred diameter of the through-holes added to the sex aids of the present invention for use with lubricating fluids is in the size range of from about 1.5 mm to about 3.5 mm, although smaller or larger diameter holes, say in the range of from about 0.5 mm to about 5 mm may work, depending on the viscosity of the fluid and the energy output of any associated vibrator or other associated stimulation. The sex aids with which the present invention can be used may be of any hard, soft or pliable material, say plastic, plastic-jelly, simulated skin, rubber, silicone and the like. The sex aids may be active or passive, say vibrating or non-vibrating. Non-limiting examples of the sex aids that may be improved by the present invention are dongs, dongs with simulated testicles, dildos, double dildos, attachable prosthetic penises, strap-on penises with or without an opposed extension, male masturbator tubes, simulated vaginas, blow-up dolls with orifices, activated simulated tongues, anal plugs, anal probes, G-spot vibrators, double dongs, penis rings with clitoral stimulators, female stimulators, and the like, all as are well known in the art. It is also apparent that any and all new sex aids may be modified for the practice of the present invention.

In one specific embodiment, a state of the art hand-held reciprocating vibrator base is connected to a stimulating element. The stimulating element is modified to have an added hollow internal chamber. At least one or more hole extends from the added hollow internal chamber in open fluid contact with the surface of the stimulating element. In operation, an off the shelf water soluble moisturizing fluid is poured into the added hollow internal chamber. When used, vibration and external air pressure causes the moisturizing fluid to egress from the chamber through the holes to lubricate the body parts with which the stimulating element is placed in contact to thereby avoid irritation or pain during sexual activities or during auto erotic sex activities, while concomitantly increasing the pleasure of the users or user and thereby meeting one of the objects of the present invention.

These and other objects of the present invention will become apparent to those skilled in the art from the following detailed description and accompanying drawings, showing the contemplated novel construction, combination, and elements as herein described, and more particularly defined by the appended claims, it being understood that changes in the precise embodiments to the herein disclosed invention are meant to be included as coming within the scope of the claims, except insofar as they may be precluded by the prior art.

BRIEF DESCRIPTION OF THE DRAWINGS

The accompanying drawings, which are incorporated in and form a part of this specification, illustrate complete preferred embodiments of the present invention according to the best modes presently devised for the practical application of the principles thereof, and in which.

DETAILED DESCRIPTION OF THE INVENTION

Figure 1:
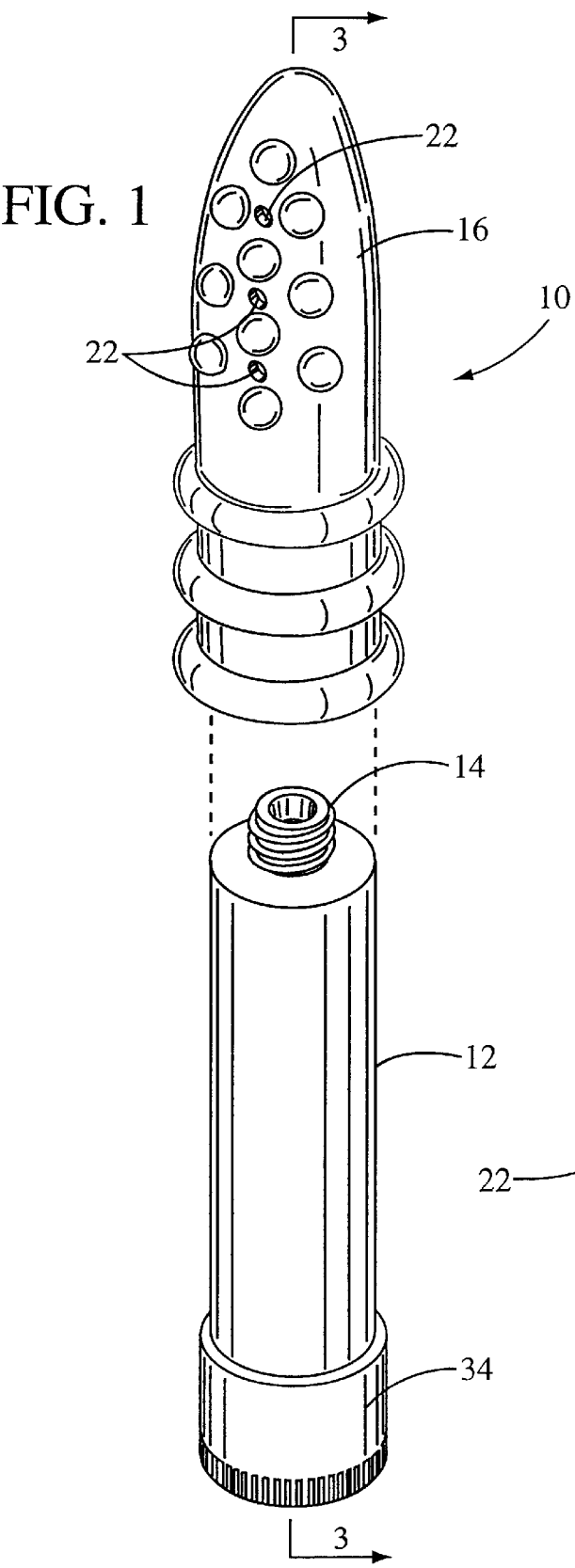
FIG. 1 shows an exploded isometric view of one preferred embodiment of a sex toy in accordance with the present invention including a hand held reciprocating vibrator base and a connecting stimulating element sex aid modified in accordance with the present invention.
Figure 2:
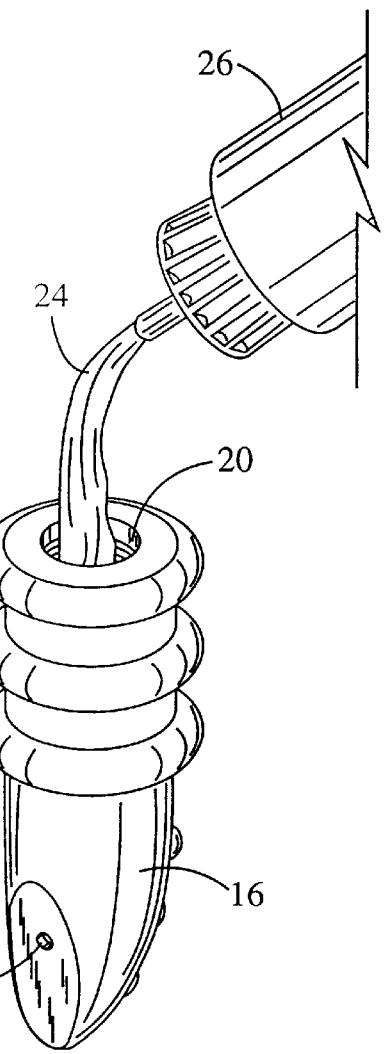
FIG. 2 shows an inverted isometric view of the stimulating element sex aid portion of FIG. 1 modified in accordance with the present invention.
Figure 3:
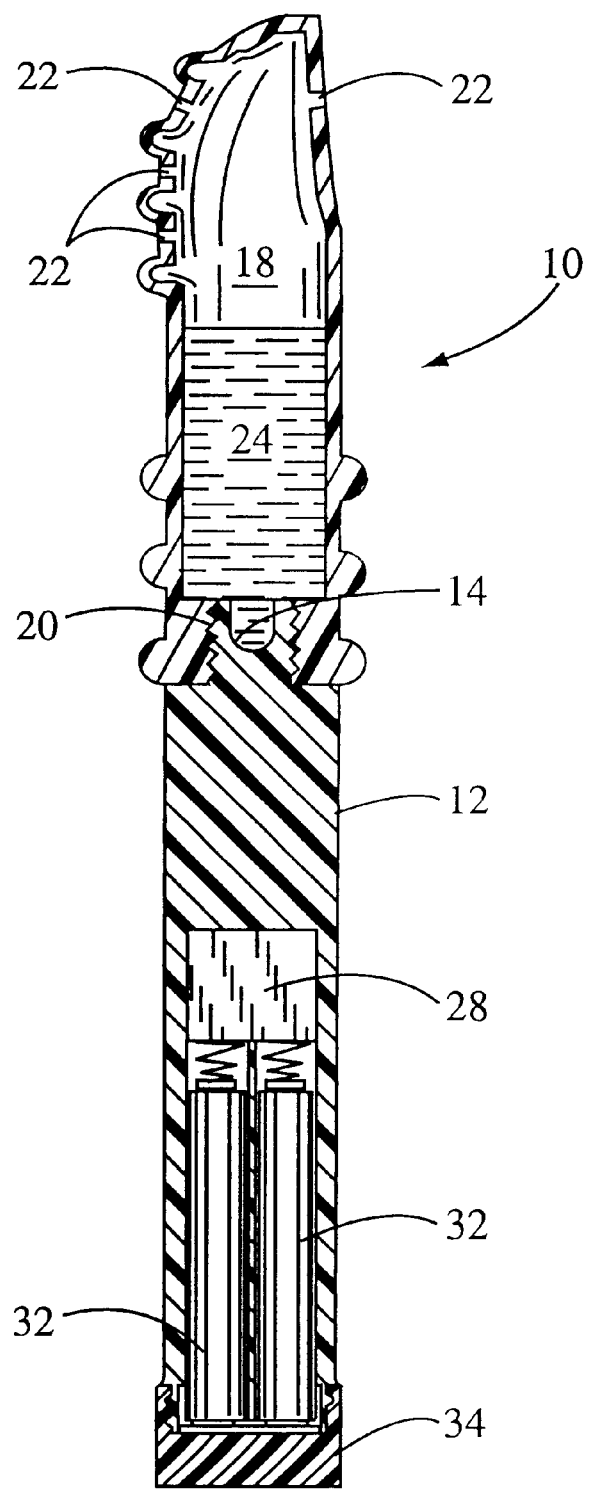
FIG. 3 shows a cross-sectional view taken along line 3—3 of FIG. 1, but including the hand held reciprocating vibrator base connected to stimulating element of a sex aid modified in accordance with the present invention.

Referring now to FIGS. 1–3, one preferred embodiment of the present invention, generally 10, a state of the art hand-held reciprocating vibrator base 12, including a standard threaded male extension 14 for connection to a stimulating element 16, is shown. Stimulating element 16 is shown to be modified to define a hollow internal chamber 18, FIG. 3, along with a standard threaded internal female receiver 20. Stimulating element 16 also includes a plurality of through-holes 22 extending in open contact with added hollow internal chamber 18 to provide open fluid contact to the surface of the stimulating element 16. Holes 22 have a diameter in the size range of from about 1.5 mm to about 3.5 mm. In operation, an off the shelf water-soluble moisturizing fluid 24 is poured from container 26 into internal chamber 18 within stimulating element 16. The size of through-holes 22 and the viscosity and surface tension of moisturizing fluid 24 is such that the moisturizing fluid 24 tends to stay within internal chamber 18 within stimulating element 16. As best shown in FIG. 3, hand-held reciprocating vibrator base 12 carries an imbedded electrically powered vibrator motor 28 that may be energized by dry cell batteries 32 removably carried within hand-held reciprocating vibrator base 12. Base cap 34 is removable to allow access to batteries 32, and also serves as a rotatable switch to turn electrically powered vibrator motor 28 on and off, and in preferred embodiments to vary the amplitude and speed of electrically powered vibrator motor 28. In their current embodiment, the exterior of both reciprocating vibrator base 12 and stimulating element 16 are constructed of rigid plastic, although modification of stimulating element 16 to soft rubber or silicone rubber is contemplated as being within the teaching of the present invention.

In operation, after moisturizing fluid 24 has been placed within internal chamber 18 of stimulating element 22, movement, vibration and external air pressure causes moisturizing fluid 24 to egress from chamber 18 through-holes 22 to lubricate the body parts with which the stimulating element 16 is placed in contact. The presence of moisturizing fluid 24 assists in avoiding irritation or pain during sexual activities or during autoerotic sex activities, while concomitantly increasing the pleasure of the users or user, and without requiring interruptions before or distractions during such activity to apply moisturizing fluid by hand or by other means.

Figure 4:
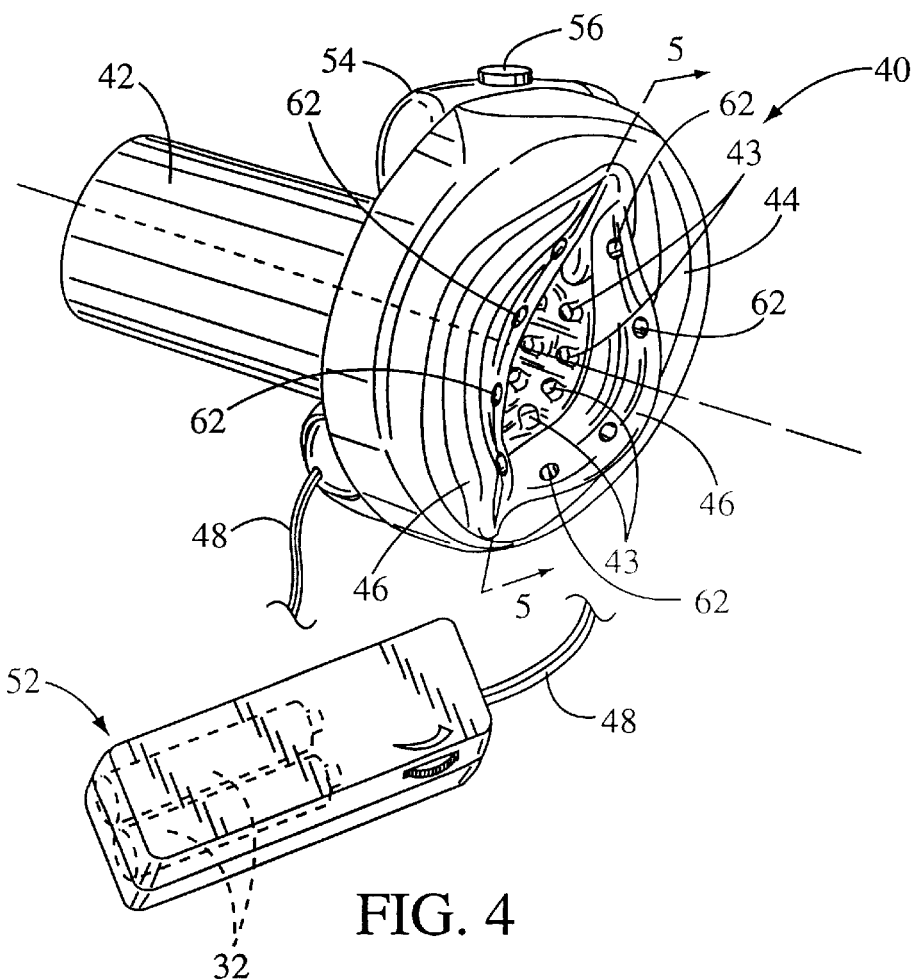
FIG. 4 shows an isometric view of another preferred embodiment in the form of a simulated vagina sex toy, to which a male masturbator tube is attached, and including an imbedded vibrating element in accordance with the present invention.
Figure 5:
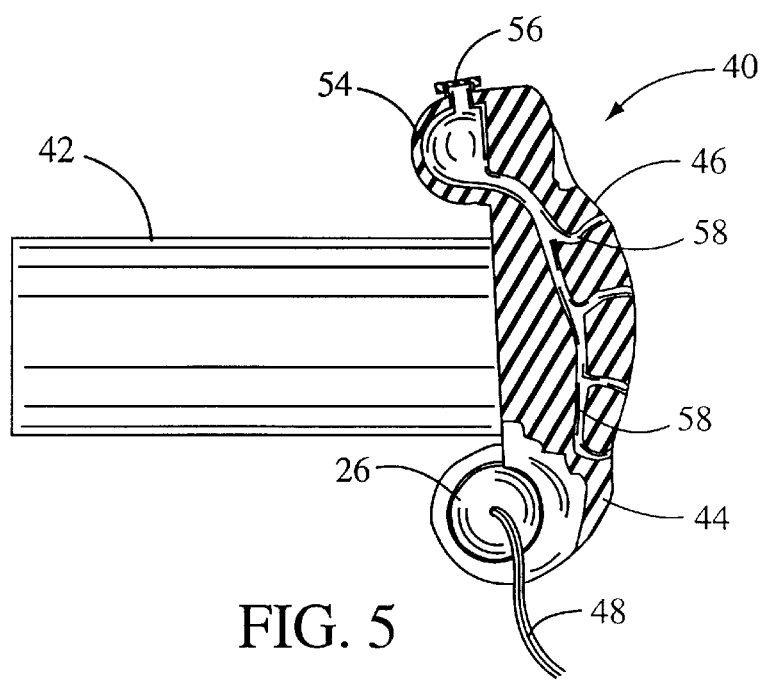
FIG. 5 shows a cross-sectional view taken along line 5—5 of FIG. 4 of the simulated vagina sex toy, but with the male masturbator tube not in cross-section in accordance with the present invention.

Now referring to FIGS. 4 and 5, another embodiment the present invention is shown. In this embodiment a simulated vagina sex toy, generally 40, is shown. In the embodiment shown a flaccid soft plastic male masturbator tube 42, including internal stimulator knobs 43 is attached. Simulated vagina portion 44 is generally toroidal in shape, and, in the embodiment illustrated, includes simulated vaginal lips 46. As best shown in FIG. 5, included in vagina portion 44 is an electrically powered imbedded reciprocating vibrating element 28 connected by wires 48 to an external battery 32 powered multi-speed battery pack 52. Also carried by vagina portion 44 is a reservoir 54 including a closure cap 56. A plurality of internal tubes 58 each extends from hollow reservoir 54 to provide open fluid contact to holes 62 at the surface of simulated vagina portion 44. As with the previous embodiment, holes 62 have a diameter in the size range of from about 1.5 mm to about 3.5 mm.

In operation, closure cap 56 is opened and an off the shelf water-soluble moisturizing fluid, not shown, is poured into reservoir 54 carried by vagina portion 44. Once again the size of through-holes 62 and the viscosity and surface tension of the moisturizing fluid is such that the moisturizing fluid tends to stay within through-holes 62 within vagina portion 44. A rotatable switch 64 integrated with multi-speed battery pack 52 is capable of turning electrically powered vibrator element 28 on and off, and in preferred embodiments, to vary the amplitude and speed of electrically powered vibrator motor 28. In operation, after moisturizing fluid has been placed within reservoir 54 of vagina portion 44, after which movement, vibration and external air pressure causes moisturizing fluid to egress from reservoir 54 through-holes 62 to lubricate the body parts with which the vagina portion 44 is placed in contact. The moisturizing fluid assists in avoiding irritation or pain during sexual activities or during autoerotic sex activities, while concomitantly increasing the pleasure of the user, and without requiring interruptions before or distractions during such activity to apply moisturizing fluid by hand or by other means.

In preferred embodiments, vagina portion 44 is composed of a jelly form of silicone plastic, and, where desired may be scented to enhance the pleasure of using the system. While reservoir 54 is shown to be connected to vagina portion 44, it may be readily seen that such a reservoir may be separate and connected, for example by tubes, to vagina portion 44.

Figures 6, 7:
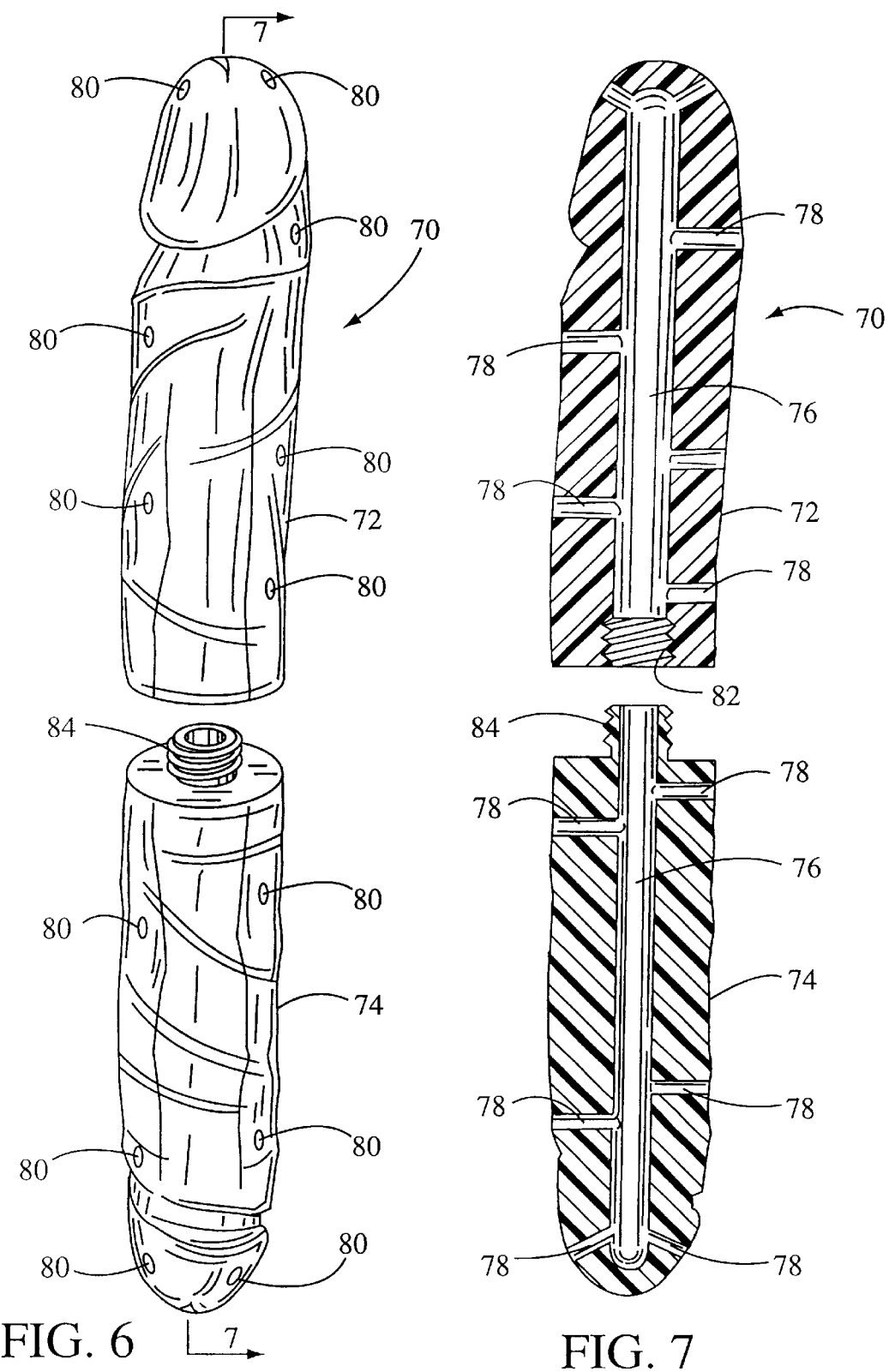
FIG. 6 shows an explode isometric view of another preferred embodiment, in this embodiment of a double dildo.
FIG. 7 shows a cross-sectional view taken along line 7—7 of FIG. 6 of the double dildo sex toy in accordance with the present invention.

Finally, referring to FIGS. 6 and 7 yet another embodiment of the present invention is shown. In this embodiment a double dildo, generally 70, is shown in an explode view. In the embodiment shown first and second dildo elements, generally 72 and 74 respectively, are shown. As best shown in FIG. 7, included in both dildo portions 72 and 74 is a hollow reservoir 76 including a plurality of tubes 78, each extending from each hollow reservoir 76 to provide open fluid contact to holes 80 at the surfaces of first and second dildo elements 72 and 74. Holes 80 have a diameter in the size range of from about 2 mm to about 5 mm.

As shown, a dildo portion 72 includes a standard threaded female internal receiver 82. Threaded female internal receiver 82 defines an annular opening leading to its hollow reservoir 76 for ease of filling its reservoir 76 with moisturizing fluid. Similarly, dildo portion 74 includes a standard threaded external male element 84. Threaded male element 84 also defines an annular opening leading to its respective hollow reservoir 76 for ease of filling that reservoir 76 with moisturizing fluid. Dildo portions 72 and 74 are preferably constructed of semi-rigid, bendable soft rubber or plastic. Unlike the previous two embodiments, double dildo 70 includes no vibrator element.

In operation, after moisturizing fluid is placed within reservoirs 76, movement and external air pressure causes moisturizing fluid to egress from reservoirs 76 through the plurality of tubes 78, to holes 80 at the surfaces of first and second dildo elements 72 and 74 to thereby lubricate the body parts with which dildo portions 72 and 74 are placed in contact. In such use, once again the moisturizing fluid assists in avoiding irritation or pain during sexual activities or during autoerotic sex activities, while concomitantly increasing the pleasure of the users or user, and without requiring interruptions before, or distractions during, such activity to apply moisturizing fluid by hand or by other means. While not shown, a central plug element may be placed in use between dildo portions 72 and 74. For use with the embodiment shown in FIGS. 6 and 7 the plug would have appropriate threaded male and female elements for use in connecting dildo portions 72 and 74 together. In the alternative, dildo portions 72 and 74 could be modified to both carry threaded female elements and the plug have appropriate threaded male elements for use in connecting dildo portions 72 and 74 together. Similarly, dildo portions 72 and 74 could be modified to both carry threaded male elements and the plug has appropriate threaded female elements for use in connecting dildo portions 72 and 74 together. The benefit of using such plugs is that they will allow one reservoir 76 in one dildo portion portions 72 or 74 to be filled and then closed with such a plug, after which the remaining dildo portion 72 or 74 to be filled and then easily connected to the already plugged dildo portion.

It is possible for the devices of the present invention to be used for other purposes, such as massage of any part of the body. Regardless of how the devices are used, they are best used if they are cleaned before and after each use.

As noted in the summary, the concept of the present invention as shown i can be easily applied to many other forms of sex aid, as listed in the summary.

The foregoing exemplary descriptions and the illustrative preferred embodiments of the present invention have been explained in the drawings and described in detail, with varying modifications and alternative embodiments being taught. While the invention has been so shown, described and illustrated, it should be understood by those skilled in the art that equivalent changes in form and detail may be made therein without departing from the true spirit and scope of the invention, and that the scope of the present invention is to be limited only to the claims except as precluded by the prior art. Moreover, the invention as disclosed herein, may be suitably practiced in the absence of the specific elements that are disclosed herein.

What I claim is:

1. A sex aid system wherein a sex aid is modified to be self lubricating, including in combination:
    a hollow chamber for carrying lubricating fluid;
    means for providing fluid connection between said hollow chamber and said sex aid;
    said sex aid including at least one surface portion intended to contact the external or internal surfaces of a user or users; and
    one or more open hole through said surface portion of said sex aid that is intended to contact the external or internal surfaces of a user or users, each said one or more open hole having a diameter such that any lubricating fluid carried within said hollow chamber tends to stay within said hollow chamber and not to exit said one or more open hole, whereby however, any lubricating fluid contained in said hollow chamber will in use, in response to motion or to vibration and in combination with external air pressure and without the need for mechanical compression means, traverse through said one or more open hole to said surface portion of said sex aid that is intended to contact the external or internal surfaces of a user or users, to thereby render said surface portion of said sex aid self lubricated and thereby avoid or diminish irritation or pain during sexual activities or during auto erotic sex activities while using said sex aid.

2. The self-lubricating sex aid system of claim 1 wherein said hollow chamber is carried by said sex aid.

3. The self lubricating sex aid system of claim 2 wherein said hollow chamber and said means for providing fluid connection are carried by and internal within said sex aid.

4. The self lubricating sex aid system of claim 1 wherein each said one or more open hole has a diameter in the size range of from about 0.5 mm to about 5 mm.

5. The self lubricating sex aid system of claim 1 wherein said surface portion of said sex aid system is composed of materials selected from the group consisting of hard material, soft material, pliable material, plastic, plastic-jelly, simulated skin, rubber, and silicone rubber.

6. The self lubricating sex aid system of claim 1 wherein said sex aid system is selected from the group consisting of dongs, dongs with simulated testicles, dildos, double dildos, attachable prosthetic penises, strap-on penises with or without an opposed extension, male masturbator tubes, simulated vaginas, blow-up dolls with orifices, activated simulated tongues, anal plugs, anal probes, G-spot vibrators, hand-held reciprocating vibrators, double dongs, penis rings with clitoral stimulators, and female stimulators.

7. The self lubricating sex aid system of claim 6 wherein a vibrator device is associated with said sex aid, and in operation external air pressure and the motion or vibration of said sex aid system causes any fluid present in said hollow chamber to exit through said one or more hole to lubricate any external or internal body parts with which said one or more hole is placed in contact.

8. The self lubricating sex aid system of claim 7 wherein said sex aid system includes a hand-held reciprocating vibrator base connected to a stimulating element, and wherein said stimulating element is modified to include a hollow internal chamber, with at least one or more hole extending from said hollow internal chamber in open fluid contact with the surface portion of said stimulating element, whereby when lubricating fluid is inserted into said hollow internal chamber vibration and external air pressure causes the lubricating fluid to egress from the chamber through said one or more holes to thereby render said surface portion of said sex aid self lubricating and to lubricate any body parts with which the stimulating element is placed in contact to thereby avoid irritation or pain during sexual activities or during auto erotic sex activities, while concomitantly increasing the pleasure of the user or users.

9. Sex aid systems which provide self lubrication for the user or users, especially at the surface or surfaces of the sex aid that contact and stimulate the external or internal erotic surfaces of the user or users, comprising:

a modified sex aid to including a fluid receiving chamber means associated with said sex aid; and at least one or more open through-hole extending from said fluid receiving chamber means to the surface or surfaces of the sex aid that contact and stimulate the external or internal erotic surfaces of the user or users of said sex aid wherein each said one or more open hole having a diameter such that any lubricating fluid carried within said hollow chamber tends to stay within said hollow chamber and not to exit said one or more open hole, whereby however, any lubricating fluid contained in said hollow hollow chamber will in use, in response to motion or to vibration and in combination with external air pressure, traverse through said one or more open hole to said surface portion of said sex aid.

10. The process of using the sex aid of claim 9 wherein a lubricating fluid is inserted into said fluid receiving chamber means and stimulated to exit from said one or more open through-hole to the surface or surfaces of said sex aid without the need for mechanical compression means.

\* \* \* \* \*